United States Patent [19]  
Oude Alink

[11] 4,085,105  
[45] Apr. 18, 1978

[54] HEXAHYDROPYRIMIDINES

[75] Inventor: Bernardus A. Oude Alink, St. Louis, Mo.

[73] Assignee: Petrolite Corporation, St. Louis, Mo.

[21] Appl. No.: 406,544

[22] Filed: Oct. 15, 1973

[51] Int. Cl.$^2$ .......................................... C07D 239/74
[52] U.S. Cl. ............................. 260/251 A; 260/251 R; 424/251; 44/63
[58] Field of Search .................. 260/251 A, 251 R

[56] References Cited

U.S. PATENT DOCUMENTS

| 2,486,648 | 11/1949 | Haury | 260/585 |
| 2,525,855 | 10/1950 | Bergmann | 260/251 R |
| 3,936,279 | 2/1976 | Alink et al. | 44/63 |

FOREIGN PATENT DOCUMENTS

74/30355  3/1974  Japan.

OTHER PUBLICATIONS

Razuvaev et al., Chemical Abstracts, vol. 50, 13904f, (1956).
Svetozarskii et al., Chemical Abstracts, vol. 55, 555f, 6486a (1961).
Armarego et al., Chemical Abstracts, vol. 71, 69950t, (1969).

Primary Examiner—Donald G. Daus
Assistant Examiner—Diana G. Rivers
Attorney, Agent, or Firm—Sidney B. Ring; Hyman F. Glass

[57] ABSTRACT

This invention relates to hexahydropyrimidines (HHP) and to the preparation of HHP by the reduction of tetrahydropyrimidines (THP). HHP is preferably prepared by reacting carbonyls, such as ketones and aldehydes, with ammonia in the presence of ammonium formate to form THP and then reducing THP to HHP. The preferred carbonyl is a cycloalkylene ketone such as cyclohexyl ketone or substituted cyclohexyl ketone.

7 Claims, No Drawings

HEXAHYDROPYRIMIDINES

In Ser. No. 292,494 filed on Sept. 27, 1972 there is described and claimed substituted 2, 3, 4, 5-tetrahydropyrimidines (THP)

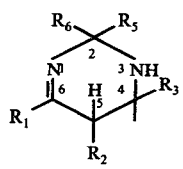

which are prepared by the following reactions:
(1) The reaction of a carbonyl compound (ketone or aldehyde) with (NH$_3$ or NH$_4$OH) and a sulfur-containing catalyst.
(2) The reaction of an α,β-unsaturated ketone and a carbonyl compound and NH$_3$ (or NH$_4$OH) without a catalyst.
(3) Reaction of an α,β-unsaturated ketone, a 1-aminoalcohol and NH$_3$ (or NH$_4$OH) without a catalyst.

In the above formula, R$_1$, R$_2$, R$_3$, R$_4$, R$_5$ and R$_6$, which may be the same or different, are hydrogen or substituted group such as alkyl, aryl, cycloalkyl, alkaryl, aralkyl, heterocyclic, substituted derivatives thereof, etc. In addition R groups may be joined in a cyclic configuration which makes the THP structure a part of the substituted group.

Alkyl includes methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, escosyl, docosyl, etc. for example having about 1-25 or more carbons such as from about 1-18 carbons, but preferably about 1-12 carbons. The term "alkyl" also includes isomers of the straight chain where branching occurs.

Cycloalkyl includes cyclopentyl, cyclohexyl, etc. and derivatives thereof such as alkyl cyclohexyl, dialkylcyclohexyl, etc.

Aryl, alkaryl and aralkyl include phenyl, alkyl-phenyl, polyalkylphenyl, chlorophenyl, alkoxyphenyl, naphthyl, alkylnaphthyl, etc., benzyl, substituted benzyl, etc.

The joining of the R groups into a ring structure include those structures derived from reactants of the general formula (CH$_2$)$_n$C = O such as cyclohexanone, cyclopentanone, substituted derivatives thereof such as alkyl-cyclohexanone, dialkyl-cyclohexanone.

I have now discovered a class of compounds which are prepared by reducing THP.

I have also discovered an unique method of preparing HHP which comprises using a formate salt such as ammonium formate. The use of ammonium formate is unique for the following reasons:
(1) In the preparation of THP from a carbonyl compound and ammonia, ammonium formate operates as a very efficient catalyst without being consumed.
(2) In the preparation of HHP from THP, ammonium formate serves as a reducing agent, yielding CO$_2$ and NH$_3$ as byproducts. It is often preferred to form ammonium formate by allowing ammonia to react with formic acid present during the initial phase of the reaction. The byproducts, produced in the process of preparing HHP from a carbonyl compound, formic acid and ammonia, are H$_2$O, CO$_2$, and NH$_3$ and are all easily removed.

The specific reaction is as follows:

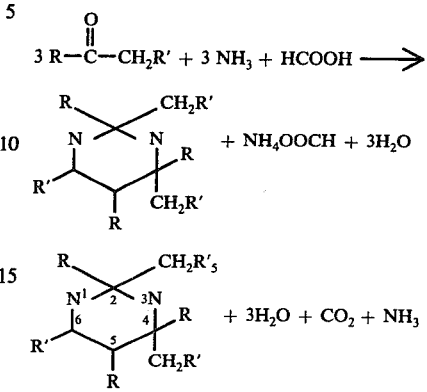

If a symmetric carbonyl compound is employed, i.e., R = CH$_2$R' a single HHP will be produced, for example in the case of cyclohexanone, the reaction may be summarized as follows:

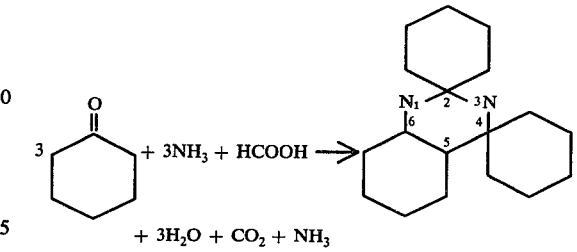

In the preferred method of this invention, the carbonyl compound is reacted with ammonia in the presence of ammonium formate (or formic acid so as to form ammonium formate in sutu) under pressure to keep the volatile components in the reaction mixture. The reaction is carried out at a temperature and time sufficient to produce THP, for example at a temperature of 20°-100° C. or higher, such as from 20°-55° C. for preferably from 2-18 hrs.

In general the molar ratio of carbonyl to NH$_3$ to formic acid is at least 3 to 3 to 1 but preferably 3 to 3-4 to 1.

After completion of the formation of THP, the reaction mixture is further heated, preferably under reduced pressure to remove H$_2$O CO$_2$ and NH$_3$ at a temperature of 40°-200° C. for 0.5 to 24 hrs. to produce HHP.

The preferred carbonyl compound is cyclohexanone. Not all carbonyl compounds can be used. For example methyl ethyl ketone (MEK) when reacted with ammonia in the presence of formic acid yields a mixture of 2,4,5,6-tetramethyl-2,4-diethyl and 2,4-dimethyl-2,4,6-triethyl-2,3,4,5-tetrahydropyrimidine which upon further reaction with ammonium formate gives a mixture of dihydropyridines, a process involving deammoniation rather than reduction of the tetrahydropyrimidine moiety. However, MEK in combination with cyclohexanone yields the HHP.

Substituted cyclohexanones can also be used. Also mixtures of cyclohexanones and other ketones or aldehydes can be used so as to yield mixtures of substituted hexahydropyrimidines.

The following examples are presented by way of illustration and not of limitation.

EXAMPLE 1

2,2,4,4-Dipentamethylene-5,6-tetramethylene hexahydropyrimidine

A mixture of 294 grams of cyclohexanone and 51 grams of 90% formic acid were placed in a pressure reactor. To the mixture was added with cooling and stirring 58.6 grams of ammonia gas over a ½ hour period. The mixture was stirred for 18 hours at ambient temperature. The resulting product was subjected to a vacuum (25 mm Mg) at 60° C. and the distillate 18 grams of unreacted cyclohexanone (6%) and water was discarded. The product was further heated for 3 hours at 120°–125° C. The resulting product 237.6 grams (86%) was identified as 2,2,4,4-Dipentamethylene-5,6-tetramethylene hexahydropyrimidine, $b_{0.5}$ 153°–155° C.

Anal. Calc.ed for $C_{18}H_{32}N_2$; C, 78.20; H, 11.67 N, 10.14 Found; C, 77.94; H, 11.74 N, 10.08

EXAMPLE 2

2,2,4,4-Dipentamethylene-5,6-tetramethylene hexahydropyrimidine

A mixture of 294 grams of cyclohexanone and 63 grams of ammonium formate were placed in a pressure reactor. To the mixture was added 41 grams of ammonia gas over a 1 hour period. The mixture was stirred for 18 hours at ambient temperature. The resulting heterogeneous mixture was heated under diminished pressure to 125° C. and kept at 125° C. for 3½ hours. The resulting product, 238 grams, was identical in all respects to the product described in example 1.

In a manner as described in example 1, HHP's were prepared from 2-methyl cyclohexanone, 3-methyl cyclohexanone, 4-methyl cyclohexanone, mixture of cyclohexanone and acetone; cyclohexanone and methyl ethyl ketone; cyclohexanone and cyclopentanone; cyclohexanone and propionaldehyde; cyclohexanone and cycloheptanone.

They are summarized as follows.

| | CARBONYL EMPLOYED | | |
|---|---|---|---|
| Ex | A | B | Molar Ratio A/B |
| 3 | 2-methyl cyclohexanone | — | |
| 4 | 3-methyl cyclohexanone | — | |
| 5 | 4-methyl cyclohexanone | — | |
| 6 | cyclohexanone | acetone | 2 |
| 7 | cyclohexanone | methyl ethyl ketone | 2 |
| 8 | cyclohexanone | cyclopentanone | 1 |
| 9 | cyclohexanone | propionaldehyde | 2 |
| 10 | cyclohexanone | cycloheptanone | 1 |

The products of the above reactions where HHP are prepared are summarized in the following table:

| RING Ex. | Position Subst. Group | 6 $R_1$ | 5 $R_2$ | 4 $R_3$ | 4 $R_4$ | 2 $R_5$ | 2 $R_6$ |
|---|---|---|---|---|---|---|---|
| 1 | | $-(CH_2)_4-$ | | $-(CH_2)_5-$ | | $-(CH_2)_5-$ | |
| 2 | | $-(CH_2)_4-$ | | $-(CH_2)_5-$ | | $-(CH_2)_5-$ | |
| 3 | | $-CH-(CH_2)_3-$ \| $CH_3$ | | $-CH-(CH_2)_4-$ \| $CH_3$ | | $-CH-(CH_2)_4-$ \| $CH_3$ | |
| 4 | | $-CH_2-CH-(CH_2)_2-$ \| $CH_3$ | | $-CH_2-CH-(CH_2)_3-$ \| $CH_3$ | | $-CH_2-CH-(CH_2)_3-$ \| $CH_3$ | |
| 5 | | $-(CH_2)_2-CH-CH_2-$ \| $CH_3$ | | $-(CH_2)_2-CH-(CH_2)_2-$ \| $CH_3$ | | $-(CH_2)_2-CH-(CH_2)_2-$ \| $CH_3$ | |
| 6 | Mixtures of Products | $CH_3$ or $-(CH_2)_4-$ | H | $CH_3$ or $-(CH_2)_5-$ | $CH_3$ | $CH_3$ or $-(CH_2)_5-$ | $CH_3$ |
| 7 | Mixtures of Products | $CH_3$ or $-(CH_2)_4-$ | $CH_3$ or H $C_2H_5$ | $CH_3$ | $C_2H_5$ | $CH_3$ | $C_2H_5$ |
| 8 | Mixtures of Products | or $-(CH_2)_4-$ $-(CH_2)_4-$ | | or $-(CH_2)_5-$ $-(CH_2)_5-$ | | or $-(CH_2)_5-$ $-(CH_2)_5-$ | |
| 9 | Mixtures of Products | or $-(CH_2)_3-$ $-(CH_2)_4-$ | | or $-(CH_2)_4-$ $-(CH_2)_5-$ | | or $-(CH_2)_4-$ $-(CH_2)_5-$ | |
| 10 | Mixtures of Products | or H $C_2H_5$ $-(CH_2)_4-$ | | or H $C_3H_7$ $-(CH_2)_5-$ | | or H $C_3H_7$ $-(CH_2)_5-$ | |
| | | or $-(CH_2)_5-$ | | or $-(CH_2)_6-$ | | or $-(CH_2)_6-$ | |

In addition THP can be prepared by the methods described in said Ser. No. 292,494 and reduced to HHP by any conventional reducing technique such as for example with sodium-ethanol, sodiumborohydride, $LiAlH_4$, sodium bisulfite, magnesium-methanol, a hydrogenation catalyst such as platinum, palladium, cobalt, nickel, etc.

EXAMPLE A

To a mixture of 294 grams of cyclohexanone and 5 grams of ammonium chloride placed in a pressure reactor was added over a 3/4 hour period 38.8 grams of ammonia gas. After the addition was completed, the mixture was stirred for 5 hours at ambient temperature. The product was taken up in toluene and the aqueous phase which separated was discarded. The toluene solution was evaporated under diminished pressure to yield 268 grams of 2,2,4,4-dipentamethylene-5,6-tetramethylene-2,3,4,5-tetrahydropyrimidine.

A sample of 27.4 grams of 2,2,4,4-dipentamethylene-5,6-tetramethylene-2,3,4,5-tetrahydropyrimidine was dissolved in 50 grams of ethanol. To the ethanolic solution was added 6.9 grams of sodium metal at such a rate that a temperature of 70°–80° C. was maintained. After the addition was completed, the mixture was heated for 1 hour at 85°–95° C. The mixture was allowed to cool to ambient temperature and water was added. The organic layer which separated was taken up in toluene. The toluene solution after washing with water was evaporated under diminished pressure to yield 22.1 grams of 2,2,4,4-dipentamethylene-5,6-tetramethylene hexahydropyrimidine identical to the product prepared in example 1.

EXAMPLE B

To a sample of 27.4 grams of 2,2,4,4-dipentamethylene-5,6-tetramethylene-2,3,4,5-tetrahydropyrimidine dissolved in 95 grams of ethanol was added 2 grams of 5% platinum/charcoal catalyst. The mixture was hydrogenated in a hydrogenator for 7 hours at an initial pressure of 40 psi of hydrogen. The catalyst was filtered off and the ethanolic solution evaporated under diminished pressure to yield 26 grams of 2,2,4,4-dipentamethylene-5,6-tetramethylene hexahydropyrimidine identical to the product described in example A.

EXAMPLE C

A sample of 81.2 grams of 2,2,4,4-dipentamethylene-5,6-tetramethylene-2,3,4,5-tetrahydropyrimidine and 32.3 grams of triethylamine were heated to 85° C. Over a 2 hour period was added 23 grams of 90% formic acid while a reaction temperature of 85° C. was maintained. After the addition was completed, the mixture was kept at 85° C. for 16 hours. Water was added and the organic layer isolated and evaporated under diminished pressure to yield 60.3 grams of 2,2,4,4-dipentamethylene-5,6-tetramethylene hexahydropyrimidine.

In summary, the hexahydropyrimidines of this invention contain at least one cycloalkylene or substituted cycloalkylene and most preferably three cycloalkylene or substituted cycloalkylene groups preferably those having a ring of 5–7 carbons and most preferably 6 carbons, i.e., cyclohexyl.

These are ideally presented by the following formulae

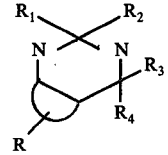

such as

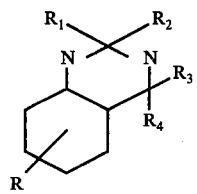

preferably

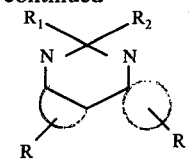

preferably

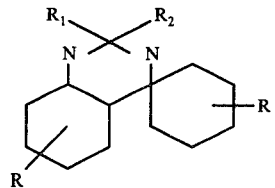

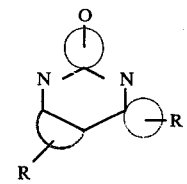

preferably

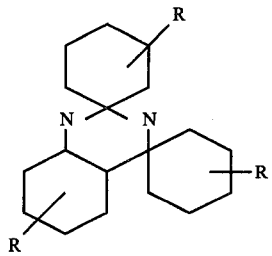

where the R's are hydrogen, alkyl, cycloalkyl, alkaryl, aralkyl, heterocyclic, and substituted derivatives thereof and the circles represent cycloalkylene structures.

The compositions of this invention are useful as fuel additives, corrosion inhibitors, biocides, i.e., bacteriocides, algecides, etc.

I claim:

1. Hexahydropyrimidine having the formula

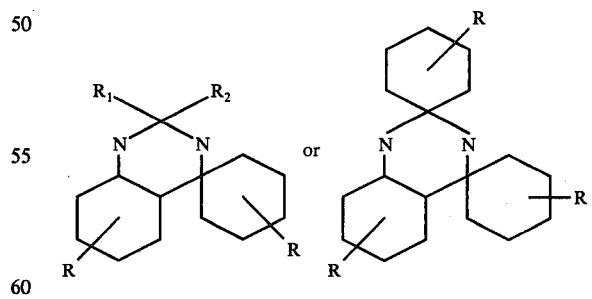

where each R is hydrogen, alkyl, aryl, cycloalkyl, alkaryl or aralkyl.

2. The hexahydropyrimidine of claim 1 which has three cyclohexyl or alkyl substituted cyclohexyl groups attached to the hexahydropyrimidine structure.

3. The hexahydropyrimidine of claim 1 of the formula

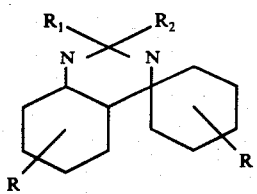

where the R's are hydrogen, alkyl, aryl, cycloalkyl, alkaryl or aralkyl.

4. The hexahydropyrimidine of claim 1 of the formula

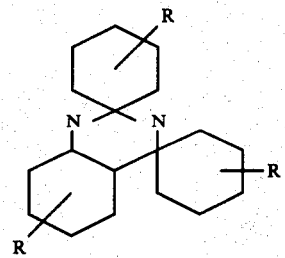

where the R's are hydrogen or alkyl.

5. The hexahydropyrimidine of claim 2 where the R's are hydrogen or alkyl.

6. The hexahydropyrimidine of claim 1 where all the R's are alkyl.

7. The hexahydropyrimidine of claim 4 which is 2,2,4,4-dipentamethylene-5,6-tetramethylene hexahydropyrimidine.

* * * * *